United States Patent [19]

Luik

[11] 4,157,922
[45] Jun. 12, 1979

[54] CLEANING APPARATUS, ESPECIALLY FOR DENTURES

[76] Inventor: Manfred Luik, Ulmer Str. 18, 7250 Leonberg, Fed. Rep. of Germany

[21] Appl. No.: 928,887

[22] Filed: Jul. 28, 1978

[30] Foreign Application Priority Data

Jul. 29, 1977 [DE] Fed. Rep. of Germany ....... 2734287

[51] Int. Cl.$^2$ .................................................. B08B 3/02
[52] U.S. Cl. .................................. 134/58 R; 134/102; 134/117; 134/197; 134/200; 366/101
[58] Field of Search .................. 134/58 R, 94–95, 134/100, 102, 117, 155, 184, 195–196, 200; 68/183; 366/101, 106

[56] References Cited

U.S. PATENT DOCUMENTS

| 1,388,249 | 8/1921 | Freter | 134/95 UX |
|---|---|---|---|
| 1,554,147 | 9/1925 | Wager | 366/101 X |
| 2,535,901 | 12/1950 | Cole | 68/183 |
| 2,788,008 | 4/1957 | Wanzer | 134/102 X |
| 2,891,561 | 6/1959 | Hagans | 134/102 |
| 3,484,995 | 12/1969 | Gordon | 134/94 X |

FOREIGN PATENT DOCUMENTS

| 806134 | 6/1951 | Fed. Rep. of Germany | 134/94 |
|---|---|---|---|
| 1093274 | 11/1960 | Fed. Rep. of Germany | 68/183 |
| 369763 | 11/1906 | France | 134/94 |
| 382972 | 11/1932 | United Kingdom | 366/101 |

Primary Examiner—Robert L. Bleutge
Attorney, Agent, or Firm—Michael J. Striker

[57] ABSTRACT

The apparatus comprises a base including an air pump with an electrically driven diaphragm and an air outlet tube passing through the wall of the base and projecting above its top surface; a separate container adapted for receiving a cleaning liquid and an object to be cleaned, the bottom of the container being provided with an inwardly projecting air inlet collar, the projecting air outlet tube snugly fitting into the air inlet collar; and a porous air distributor mounted on the air inlet collar within the container to distribute minute air bubbles throughout the entire cleaning space in the container and to prevent leakage of the cleaning liquid when the container is removed from the base. An auxiliary capsule adapted to receive the object to be cleaned is insertable into the container. Devices for regulating the amount of the air supplied to the liquid can be added to the apparatus.

10 Claims, 2 Drawing Figures

CLEANING APPARATUS, ESPECIALLY FOR DENTURES

BACKGROUND OF THE INVENTION

The invention relates to an apparatus for cleaning objects, particularly dentures, by means of air bubbles moving through a cleaning liquid in which the object is immersed.

More particularly, this invention relates to a cleaning apparatus including a base, an air pump arranged within the base and having an air outlet passing through the base and projecting thereabove, and a separate cleaning container adapted for receiving the cleaning liquid and the object to be cleaned and being removably supported on the base and communicating with the air outlet of the pump.

It is known from the German Pat. No. GM 76 22 513 to supply air from a pump outlet through a flexible conduit having at its free end a nozzle that is to be introduced into a container from above. When displacing the container from the base, the conduit has also to be removed and for the cleaning action it has to be reinserted in the container and held in its proper working position. The disadvantage of this design is the fact that the air stream emanating from the nozzle cannot encompass the whole denture to be cleaned and for this reason during the cleaning process the flexible conduit has to be held by hand and moved in the container. The air is discharged through the nozzle in relatively large bubbles that cannot uniformly disperse in the liquid. As a result the manipulation of this known apparatus is complicated and does not provide sufficient cleaning effect.

SUMMARY OF THE INVENTION

It is therefore a general object of the present invention to overcome the aforementioned disadvantages.

More particularly, it is an object of the invention to provide an improved cleaning apparatus of the above-described type which operates automatically.

An additional object of the invention is to provide an improved cleaning apparatus which is efficient and reliable in its function.

In keeping with these objects, and others which will become apparent hereafter, one feature of the invention resides, in a cleaning apparatus having a separate cleaning container and a base including an air pump, in a combination comprising an air inlet provided in the wall of the cleaning container and being disconnectably and sealingly engageable with the air outlet from the air pump when the container is placed in its working position on the base, and valve means arranged in the container and cooperating with the air inlet to prevent leakage of the cleaning liquid when the container is removed from the base.

The invention makes it possible to remove the beaker (container) from the base and fill it with a cleaning liquid in usual manner. The object to be cleaned, such as a denture, can be conveniently inserted into the beaker from above. As soon as the container is placed in its working position on the base, it forms therewith a complete and functionally united apparatus. The air supplied by the pump is delivered immediately below the denture to be cleaned and has, therefore, an optimum cleaning effect, and the apparatus works by itself without any assistance so long as desired.

The valve means that prevents the discharge of the liquid when the container is disconnected can be either a separate non-return valve or it can also be formed by the distributor of the supplied air which is made in such a manner that it permits the passage of the air but prevents the discharge of the liquid. This effect can be achieved, for example, by providing a distributor having particularly fine pores. The finely porous configuration of the distributor contributes also to the creation of extremely minute bubbles of air that propagate into the entire body of liquid contained in the container instead of only rising quickly upwardly. Consequently, the minute bubbles emanating from the face surface and from lateral surfaces of the distributor fill up the entire cleaning space within the container and cleaning action is thereby quick and effective.

It is particularly advantageous if a separate capsule for accommodating a denture to be cleaned is inserted into the cleaning space of the container, the capsule having a perforated removable lid that during the cleaning process is directed downwardly and also having an opening in its bottom that in the cleaning position is directed upwardly. The size of the capsule is such as to occupy most of the cleaning space in the container. The capsule facilitates the insertion and particularly the removal of the cleaned denture. In a modification, the bottom of the capsule is perforated and during the cleaning process is placed directly on the distributor so as to form with the latter a support for the dentures in the cleaning space thus eliminating the need for a separate support.

It can also be of advantage if a time switch is provided on the base to control the operation of the air pump and which switches off the apparatus when a cleaning period, defined from experience, has expired. Furthermore, it can be advantageous to provide a feeding device mounted also on the base to deliver at will a definite amount of cleaning agent into the cleaning space. Preferably, the feeding device is connected to the interior of the container in similar manner as the air outlet of the air pump so as to insure a disconnectable sealing union when the container is positioned on the base.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
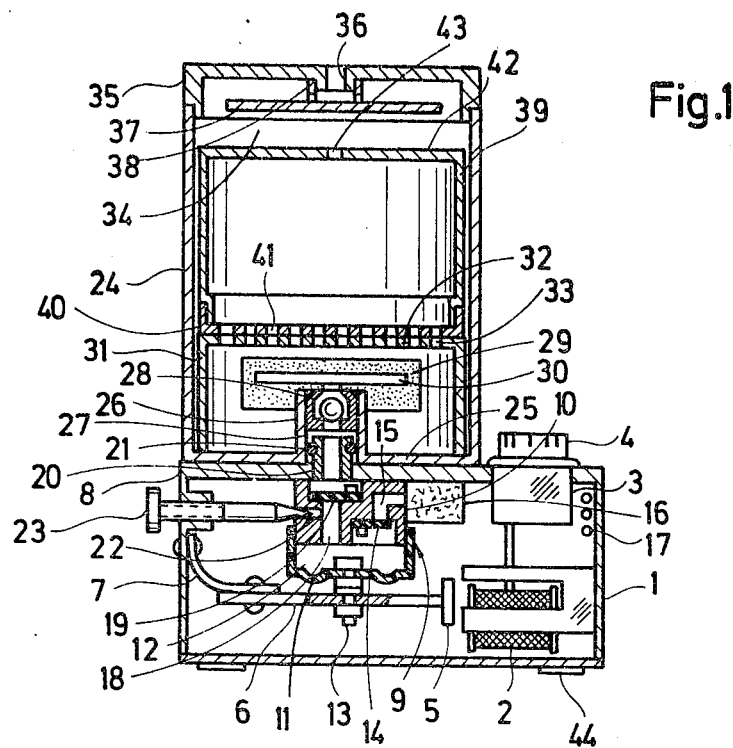
FIG. 1 is a sectional side view of one embodiment of the cleaning apparatus of the present invention.

In the example of the cleaning apparatus shown in FIG. 1, base 1 contains solenoid 2 energized by alternating current and controlled by a time switch 3. The time switch is adjustable by a control knob 4 to activate the solenoid 2 for a desired cleaning period. An armature 5 is arranged opposite the core of the solenoid 2 and is supported for a vibrational movement on an arm 6 that is secured to a wall of the base 1 by means of a spring 7.

An air pump 9 is mounted to the cover plate 8 of the base 1. The pump consists of a pump body 10 provided with air inlets and outlets and corresponding valves and supports at its bottom a membrane 11 defining with the pump body a pumping space 12. The membrane is connected to the vibrating arm 6 by means of a bolt 13. An air intake channel 15 connects the pumping space 12 via a suction valve 14 and an air filter 16 to the interior of the base 1 and through openings 17 in the base communicates with the outer atmosphere. An air outlet 18 in the pump body is provided with a pressure valve 19 and communicates with a short connecting pipe 20 projecting above the cover plate 8 of the base 1. The outer surface of the connecting pipe 20 is provided with a sealing ring 21. A transverse boring 22 connects the air outlet 18 with the interior of the base 1 and the tip of an adjusting screw 23 mounted in a side wall of the base 1 projects into the boring 22 and according to its position it closes more or less the opening 22. Both the suction valve 14 and the pressure valve 19 have respectively a flap of elastic material acting as the closing member.

A separate container 24 in, e.g. the form of a beaker is supported on the base 1. The bottom 25 of the container has an inwardly projecting collar 26, the interior of which defines a passage 27 snugly fitting the outer surface of connecting pipe 20 and its sealing ring 21. In this embodiment, a non-return valve 28 in the form of a ball valve is mounted in the upper portion of the passage 27 of the collar 26. A distributor 29 composed of a porous material and having a hollow space 30 is fittingly supported on the collar 26 within the container 24. The hollow space of the distributor 29 communicates through the passage 27 with the air outlet 18 of the pump 9. A beaker-like support 31 having its bottom provided with a plurality of perforations is put in inverted position into the container 24 so as to rest with its upper rim on the bottom of the container 24. The bottom 32 of the support provided with a plurality of perforations 33 is positioned above the distributor 29 and extends substantially over the entire cross-section of the cleaning space 34 within the container 24.

A removable lid 35 closes the open top of the container 24 and is provided at its center with a ventilation opening 36. The ventilation opening is covered from the inside by a spray shielding plate 37 that prevents water from spurting out; the holder of the plate, however, is provided with openings for permitting the access of air.

A capsule 39 can be introduced into the cleaning space 34 and is adapted for receiving the objects to be cleaned. The capsule 39 extends substantially over the entire cross-section of the cleaning space and is also introduced therein in an inverted position in which a lid 40 having a plurality of perforations 41 rests on the perforated bottom of the support 31. The bottom 42 of the capsule is provided with a central hole 43 to permit the escape of air.

Base 1 is provided with non-slidable legs 44 so that it might be positioned on a support or suspended in a conventional manner on a wall, for example inserted into a wall holder (not shown). Container 24 is removed from the base, opened and filled up with water from a faucet. Non-return valve 28 prevents safely the discharge of the water. A few drops of a cleaning or disinfection agent can also be added.

Lid 40 is removed from the top of the cassette 39 and the object to be cleaned is inserted therein; the cassette is then closed and inserted in an inverted position into the cleaning space 34. Thereafter, lid 35 is applied on the container 24 and the collar 26 is brought into engagement with the connecting pipe 20 to the air outlet 18 of the base 1. In this manner the container 24 is seated in a center position around the connecting pipe 20. The annular seal 21 prevents any leakage of the cleaning liquid or of the air.

Thereupon the time switch 3 is actuated and electric current is supplied to solenoid 2 for a desired time period during which the armature 5 vibrates and drives membrane 11 of the air pump. The membrane pumps in a known manner air through the air filter 16 into the distributor 29. From the interior of the distributor the air penetrates through the finely porous walls of the distributor and is distributed in a finely dispersed condition through the entire body of cleaning liquid present in the perforated support 31. The finely distributed air forms numerous tiny bubbles that penetrate through holes 33 and 41 in the interior of the cassette 39 where they bring water in motion and by virtue of their surface effect they quickly complete the cleaning of the present object. The air then escapes through the hole 43 in the bottom of the cassette and therefrom through the ventilation opening 36 in the lid of the container 24 into the atmosphere. During the cleaning process the cassette can rise or lower in accordance with the height of the water level in the cleaning space 34 and the amount of the supplied air. As a consequence of this vertical movement of the cassette, the object being cleaned is always in the range of the water level where the cleaning effect is maximum.

After completion of the cleaning the container 24 is removed from the base 1. The cassette 39 is taken out and is rinsed together with its contents under running water and thereafter the cleaned object is removed.

The cleaning apparatus of this invention can also effectively operate without the cassette 39 so that lower demands are made on maintenance. Container 24 can be handled as a beaker and can be conveniently filled up and washed under a water faucet; the object to be cleaned is then placed immediately on the support 31.

By suitably designing the distributor 29, the latter prevents any leakage of water downwardly and the one-way valve 28 can be dispensed with.

If the setting screw 23 is completely turned in, so it closes the opening 22 and the full amount of air delivered by the air pump is blown into the cleaning space. If this amount is excessive, the setting screw is turned out of the opening and a portion of the air is permitted to escape into the outer atmosphere. If the air pump is designed and dimensioned for a one-purpose use, the regulating device for the amount of the supplied air can also be dispensed with.

Figure 2:
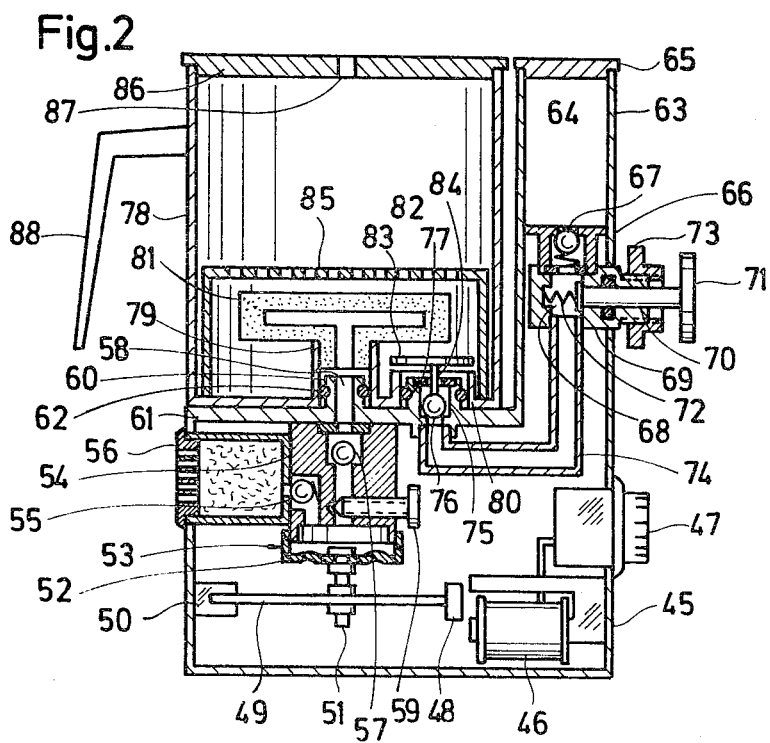
FIG. 2 is a sectional side view of another embodiment of the present invention.

In the embodiment according to FIG. 2, the cleaning apparatus has a base 45 provided, similarly as in the preceding example, with a solenoid 46 controlled by a time switch 47. An armature 48 is mounted on a vibrating arm 49 that is anchored in a projection 50 of the base and connected by means of bolt 51 to a membrane 52 of an air pump 53. Pump body 54 comprises a suction valve 55 communicating through an air filter 56 with the outer atmosphere, and further comprises an air outlet 58 with a pressure valve 57. Both valves 55 and 57 are ball valves. A setting screw 59 projects into the air outlet and regulates thus the air flow according to the desired amount of air to be supplied by the pump. The air outlet 58 opens into a short connecting pipe 60 that projects over the cover plate 61 of the base 45 and is provided with a sealing ring 62. Base 45 in this embodiment is provided with an upwardly projecting attachment 63 including a storing container 64 into which cleaning liquid is applied and closed by a removable lid 65. The bottom of the storing container 64 is formed by a feeding device 66 consisting of a suction valve 67 communicating through a pumping space 68, a conduit 74 and a pressure valve 76 with the interior of the cleaning container 78. The pumping space 68 is formed in a housing 69 that also includes a lateral boring in which a piston 70 is sealingly guided for reciprocal movement. The outwardly projecting end of the piston 70 is provided with an actuation disc 71 and a tension spring 72 located in the pumping space urges the piston 70 outwardly. A setting nut 73 is screwed on an outwardly projecting portion of the housing 69 to adjust the stroke of the piston 70. The suction conduit 74 terminates also in a short connecting pipe 75 formed in the cover plate 61 of the base 45 and the outer side walls of the connecting pipe are provided with a sealing ring 77.

The beaker-shaped cleaning container 78 rests on the top plate of the base 45 and its bottom is provided with inwardly projecting collars 79 and 80 that are arranged so as to sealingly receive the short connecting pipes 60 and 75 of the base 45 when the container 78 is brought into its operating position on the base. The downwardly projecting attachment on the distributor 81 snugly engages the collar 79 and, as mentioned above, the other collar 80 is provided with a non-return valve 82. A disc-shaped closing member 83 is connected to a lifting rod 84 that projects downwardly through the collar 80 and the connecting pipe 75 as far as to the ball of the pressure valve 76. A beaker-like support 85 corresponding to the support 31 of FIG. 1 is inserted in inverted manner into the cleaning container 78 so that the perforated bottom of the support 85 is situated above the distributor 81. A lid 86 having a venting opening 87 closes the open top of the cleaning container 78 and a handle 88 facilitates the manipulation.

To charge the container 78 with water, it is first removed from the base 45. The distributor 81 and the non-return valve 82 prevent any water leakage. The charged container is placed again into its operative position on the base 45 whereby its collars 79 and 80 engage sealingly the short connecting pipes 60 and 75. When the container 78 rests on the top plate of the base 45, the lifting rod 84 abuts against the ball-shaped closing member of the pressure valve 76 and the non-return valve 82 is opened. By pressing the actuation disc 71 of the piston 70 the latter discharges cleaning liquid from the pumping space 68 through the conduit 74 and through the pressure valve 76 into the interior of the cleaning container 78. As soon as the disc 71 is released, the tension spring 72 displaces the piston 70 outwardly so that the latter sucks cleaning liquid from container 64 through the suction valve 67. The quantity of the supplied liquid is determined by the stroke of the piston 70 that has been previously set by the setting nut 73.

Thereafter the solenoid 46 is switched on and the subsequent operation corresponds to that as described in connection with FIG. 1.

Instead of water another cleaning liquid can, of course, be employed in containers 24 and 78 in accordance with cleaning requirements for a particular object. By suitably designing the distributor 81 or 29, the latter can serve by itself as a support for the object to be cleaned; for this purpose, the top surface of the distributor can be provided with projections on which the object rests. Due to the fact that no high pressures or strong loads take place in the cleaning apparatus of this invention, its component parts can be manufactured mostly of a plastic material, particularly by a spraying process that permits an economic manufacture.

It will be understood that each of the elements described above, or two or more together, may also find a useful application in other types of constructions differing from the types described above.

While the invention has been illustrated and described as embodied in specific examples of the cleaning apparatus, it is not intended to be limited to the details shown, since various modifications and structural changes may be made without departing in any way from the spirit of the present invention. For example, the amount of air supplied by the air pump can be regulated, instead of mechanical setting screws, by means of electrical or electronic devices that supply more or less electrical energy to the driving solenoid. In many cases it is sufficient to provide a time switch having only two ranges and it is also possible to use the device of this invention without the time switch since an exact timing is not required and the user of the apparatus will recognize from experience how much time is needed for cleaning a particular object.

What is claimed as new and desired to be protected by Letters Patent is set forth in the appended claims:

1. In a cleaning apparatus including a base, an air pump arranged within the base and having an air outlet, and a separate container adapted for receiving a cleaning liquid and an object to be cleaned, a combination comprising, an air inlet provided in said container and adapted for snugly fitting said air outlet in said base when said container is placed in its operative position on said base; and valve means disposed at said inlet to prevent leakage of said cleaning liquid when said container is removed from said base.

2. A combination as defined in claim 1, wherein said air outlet communicates with a short connecting pipe projecting from said base, and said air inlet is in the form of a collar defining a passage snugly surrounding said short connecting pipe.

3. A combination as defined in claim 2, wherein a non-return valve is arranged in said passage of said collar to admit air from said air outlet into said container.

4. A combination as defined in claim 2, further including a distributor made of finely porous material and defining a cavity communicating with said air inlet, said distributor being supported on said collar and extending over a major part of horizontal cross-sectional area in the cleaning space in said container to distribute minute air bubbles through the whole body of cleaning liquid present in said cleaning space.

5. A combination as defined in claim 4, wherein said distributor defines a horizontal top surface extending over the major part of the cross-sectional area of said cleaning space and being applicable as a supporting surface for the object to be cleaned.

6. A combination as defined in claim 4, further including a separate cassette adapted for accommodating objects to be cleaned and insertable in an inverted position into said container to face during the cleaning process said air distributor, the bottom of said cassette having a venting opening for discharging the used air.

7. A combination as defined in claim 1, further including an electromagnetic drive means for said air pump and a time switch for setting an operational period, and a regulating device for controlling the amount of air supported by said air pump.

8. A combination as defined in claim 1, wherein said base includes a feeding device for delivering predetermined doses of the cleaning liquid into said container.

9. A combination as defined in claim 8, wherein said feeding device comprises a liquid storing container, a hand-operated feeding pump communicating with said container through a suction valve and with said cleaning container through a pressure valve.

10. A combination as defined in claim 9, wherein said base has a second connecting pipe communicating via a suction conduit with said feeding pump and being provided with said pressure valve, and said cleaning container having a second inlet snugly fitting said second connecting pipe when said container is brought in operative position on said base.

* * * * *